(12) United States Patent
Carney

(10) Patent No.: US 7,303,771 B2
(45) Date of Patent: Dec. 4, 2007

(54) ALFALFA SPROUT POWDER BASED SUPPLEMENT

(76) Inventor: Stephen Truesdale Carney, 191 Spring Rd., North Kingstown, RI (US) 02852

( * ) Notice: Subject to any disclaimer, the term of this patent is extended or adjusted under 35 U.S.C. 154(b) by 0 days.

(21) Appl. No.: 10/800,608

(22) Filed: Mar. 15, 2004

(65) Prior Publication Data

US 2005/0202062 A1    Sep. 15, 2005

(51) Int. Cl.
*A61K 36/00* (2006.01)
*A61K 31/355* (2006.01)
*A61K 31/34* (2006.01)
*A61K 31/59* (2006.01)

(52) U.S. Cl. .................. 424/725; 514/52; 514/458; 514/474; 514/167

(58) Field of Classification Search .................. None
See application file for complete search history.

(56) References Cited

U.S. PATENT DOCUMENTS

2002/0172721 A1* 11/2002 Boulos et al. .............. 424/646

OTHER PUBLICATIONS

Vitacost.com; NSI Synergy Multi-vitamin 180 Caps; URL< http://web.archive.org/web/20030201111524/www.vitacost.com/products/brandsaz/nsiprods/bmod/Synergy/Mens.cfm?homepage=yes, 2 pages.*

The World's Healthiest Foods: Feeling Great; URL<www.whfoods.com/nutrientstoc.php, one page.*

Dr. Duke's Phytochemical and Ethnobotanical Databases: Medicago sativa subsp. sativa (Fabaceae)—Alfalfa, Lucerne, URL<www.ars-grin.gov/cgi-bin/duke/farmacy2.pl> pp. 1-6.*

Story et al. Interactions of Alfalfa Plant and Sprout Saponins With Cholesterol In Vitro and In Cholesterol-Fed Rats; Am J. Clin. Nutr. 1984; 39, pp. 917-929.*

Webb, d. New, Natural Ways to Fight Cholesterol; Prevention, Sep. 2001, vol. 53, 9, p. 68 (pp. 1-3 from ProQuest database).*

Rink, L.M.D.,F.A.C.C, Folic Acid and Alfalfa the Fall Study; Feb. 12, 2003 URL<http://www.sproutequipment.com/Nutrition/research/folic_acid_and_alfalfa.htm> pp. 1-3.*

Muldoon, K. Busy Lawer Connects Spiritual, Physical Aspects of Life . . . The Oregonian, Portland, OR., Aug. 12, 1996 p. C. 03, pp. 1-2 of ProQuest.*

* cited by examiner

*Primary Examiner*—Patricia Leith

(57) ABSTRACT

The present disclosure relates to the novel nutritional methods and compositions containing essential alfalfa sprouts powder which reduces certain risk factors of cardiovascular disease specifically an individual's C-reactive protein, LDL-cholesterol, homocysteines and triglycerides while increasing an individual's HDL-cholesterol level.

9 Claims, No Drawings

ALFALFA SPROUT POWDER BASED SUPPLEMENT

CROSS-REFERENCE TO RELATED APPLICATIONS

Not applicable.

STATEMENT REGARDING FEDERALLY SPONSORED RESEARCH OF DEVELOPMENT

Not applicable.

REFERENCE TO SEQUENCE LISTING, A TABLE, OR A COMPUTER PROGRAM LISTING COMPACT DISK APPENDIX

Not applicable.

BACKGROUND OF THE INVENTION

1. Field of the Invention

The present disclosure relates to novel nutritional methods and compositions containing essential alfalfa sprouts powder which reduces certain risk factors of cardiovascular disease specifically an individual's C-reactive protein, low-density lipoproteins ("LDL") cholesterol, homocysteines and triglycerides while increasing an individual's high-density lipoproteins ("HDL") cholesterol level.

2. Field of Related Art.

In 1908 Dr. Adolf Otto Windaus discovered, "the property of complex formations between saponins and cholesterol." It has been known for many years that saponins form insoluble complexes with cholesterol.

Studies showing saponins reducing cholesterol:

| Griminger | chickens | 1958 |
| Cheeke | hens | 1971 |
| Backer | rats | 1972 |
| Kritchevsky | rats | 1975 |
| Malinow | rats | 1977 |
| Malinow | monkeys | 1978 |
| Oakenfull | hamsters | 1982 |
| Lutomski | rats | 1983 |
| Ivanov | cats | 1987 |
| Hansel | mice and cats | 1988 |
| Sauvaire | dogs | 1991 |

Work by Cheeke has shown triterpene glycosides in feed given to hens decrease the amount of cholesterol in both blood and tissues. This may be the result of the formations of a cholesterol-triterpene glycoside complex in the digestive tract which is not reabsorbed or there is a possibility of a direct effect on cholesterol metabolism.

Kritchevsky, et al, appear to have been the first to suggest that the saponins in alfalfa were the cause of the lower plasma cholesterol levels in rats fed an alfalfa based diet.

In 1978 Malinow, et al, have since provided conclusive evidence that the saponins in alfalfa are indeed responsible by demonstrating the cholesterol-lowering activity of isolated alfalfa saponins.

Saponins have relatively large molecular weight and are of high polarity. In 2000, the United States Army chemical and biological group completed a study of 2600 known saponins. *Spectroscopic Data of Saponins The Triterpene Glycosides*, Vigar Uddin Ahmad and Anwer Basha. It presented the molecular makeup of the 13 different saponins found in alfalfa-medicago saponins 1, 2, 5, 6, 7, 8, 9, 10, A, B, F, P1 and P2. Of the 2600 saponins in the study only one, medicago saponin A, forms a complex with the cholesterol membrane.

Triterpene saponins have the ability to strengthen veins and decrease blood vessel permeability. Saponins may interact with cholesterol present in the cell membrane, altering the cell function.

Alfalfa saponins are reported to depress concentrations of lipids and cholesterol in the livers of mice. It is thought that medicagenic acid glycosides are responsible for these effects.

As a consequence of these observations, the suggestion has been made that foods rich in saponins may reduce the risk of heart disease.

All saponins have in common the attachment of one or two sugar chains (seldom three) to the aglycone. Alfalfa is one of three known plants to have three sugar chains. The aglycone or non-saccharide portion of the saponin molecule is called the genin or sapogenin. Most saponins have 22-26 atoms in their molecule. Alfalfa has a 30 carbon atom molecule, a true triterpene saponin. Alfalfa is a tridesmoside triterpene glycoside.

It has been established that saponins with acidic sapogenins (ones that exhibit carboxylic groups) bind cholesterol in vitro, while saponins with neutral sapogenins do not form complex cholesterol. However saponins with neutral sapogenins can form complexes with bile salts more easily than acidic saponins. Therefore, there is a synergism with acidic and neutral saponins relative to the reduction of cholesterol. The only known edible plant to possess both kinds of saponins is alfalfa.

The bile acids are thus diverted from the enterohepatic cycle and lost by fecal excretion, thus lowering plasma and liver levels.

The LDL fraction contributes to deposition of cholesterol in the artery wall. The HDL fraction is antiatherogenic or protective and through a process of reverse transportation, mobilizes the cholesterol out of the body for excretion.

C-reactive protein (CRP) levels have been shown to predict incident myocardial infarction, stroke, peripheral arterial disease, and sudden cardiac death. In terms of clinical application, CRP seems to be a stronger predictor of cardiovascular events than LDL cholesterol. To date over a dozen prospective epidemiological studies carried out among individuals with no prior history of cardiovascular disease demonstrate that a single, non-fasting measure of CRP is a strong predictor of future vascular events. A recent study of 28,000 women revealed CRP is a better predictor of cardiovascular events than LDL. Without inflammation, individuals have CRP levels below 1 mg/l; a reading over 3 mg/l is a reliable predictor of future cardiac events. In one study recently, CRP was a strong predictor of risk even 20 years after initial blood samples were obtained. There is virtually no way to predict CRP levels on the basis of HDL, LDL, or total cholesterol. CRP levels are normally less than 10 mg/l but may be at 100 or more because of major infection, trauma, or acute hospitalization. Patients can use their CRP levels as an inflammation fitness score to monitor improvement in their cardiovascular health. In March 2002, as part of an American Heart Association recommendation from a 1998 meeting, a workshop on inflammatory markers and cardiovascular disease convened in Atlanta, Ga. It reported that the best evidence to date supports the use of C-reactive protein as an independent predictor of increased coronary risk. CRP should be supported by levels of HDL, LDL, total cholesterol, triglycerides, and homocysteines.

Medicagenic acid derivatives, isolated from alfalfa, exhibited potent fungistatic effects against several plant pathogens and human dermatophytes and were fungicidal against medically important yeasts, showing a most impressive activity against cryptococcus neoformans. This was the result of the gluco derivative of medicagenic acid, compound G2.

The effectiveness of compound G2 was evaluated by clinical examination, microscopy and culture of skin scrapings. These three criteria are used routinely to evaluate the therapeutic activity of topical drugs on human skin. In two sets of experiments within two weeks (12 to 15 applications), 80% of the infected lesions treated with compound G2 were cured, compared to 20% of the untreated lesions on the same animals, which healed spontaneously. These results show marked topical efficacy.

While in some cases, it was suggested that the sapogenin rather than the intact saponin is important for the antimyotic (fungal) activity, it was shown in others that the sugar part significantly contributes to the activity.

Alfalfa and its resistance to fungal infections demonstrated the important contribution of medicagenic acid (MA), the major saponin isolated from alfalfa, to antimyotic activity.

It was shown that the plant pathogen sclerotium rolfsis, possessing a high cholesterol content in cell membranes, was more sensitive to alfalfa saponin extract than fungi having lower cholesterol contents in their membranes.

In a few cases, the changes in sugar moiety are of marginal importance. In all other cases, however, the data strongly suggests that the presence of the same component and its nature affected the anti-fungal activity although, except in one case, the saponins tested had no advantage over compound G2.

The higher efficacy of saponins containing MA was explained by their capacity to form insoluble complexes with sterols.

The overall results indicate that after further development, compound G2 might be a potent agent in the treatment of fungal infections.

In conclusion, there appear to be two mechanisms by which saponins can affect cholesterol metabolism. The first is that some saponins, with particularly defined structural characteristics, form insoluble complexes with cholesterol (as, for example, in the well known precipitation of cholesterol by digitonin). Complexation in the gut then inhibits cholesterol absorption. The second, saponins can also affect cholesterol metabolism indirectly by interfering with the enterohpatic circulation of bile acids. Some saponins form large mixed micelles with bile acids. These can have molecular weights of several millions and the reabsorbtion of the bile acids from the terminal ileum is effectively blocked. Bile acids are thus diverted from the enterohepatic cycle and lost in fecal excretion. This loss is then offset by increased synthesis from endogenous cholesterol, resulting in lower plasma and liver levels.

The binding of primary bile acids by saponins also may be significant in preventing colon cancer, by reducing their availability to form secondary bile acids via hindgut microbial activity. Saponins also bind to cholesterol and prevent cholesterol oxidation in the colon. Oxidized cholesterol products are promoters of colon cancer. Thus, dietary saponins may have beneficial effects against two major health problems: coronary heart disease (by hypocholesterolmeic activity) and colon cancer (by sequestering bile acids).

BRIEF SUMMARY OF THE INVENTION

The present invention relates to a method of reducing certain risk factors of cardiovascular disease using an alfalfa sprout powder based supplement ingested orally by an individual or used as a food additive. In an advantageous form of the invention, the alfalfa sprout powder based supplement is administered at a dose of between 1000 and 2000 mg per day.

The present invention is also a pharmaceutical composition comprising of alfalfa sprout powder and folic acid with a pharmaceutically acceptable carrier. In a preferred embodiment, the composition comprises 550 mg of alfalfa sprout powder per capsule or tablet. In another preferred embodiment, the composition comprises of alfalfa sprout powder and at least one additional ingredient. In a most preferred embodiment, this ingredient is folic acid, B-12 and B-6.

It is another feature of the present invention that the alfalfa sprout based supplement may be supplied orally to an individual in order to reduce certain risk factors of cardiovascular disease.

It is another feature of the present invention that the alfalfa sprout based supplement may be added to foods during their processing.

Other objects, features and advantages of the present invention will become apparent to one of skill in the art after review of the specification and claims.

DETAILED DESCRIPTION OF THE INVENTION

The present invention relates to an alfalfa sprout powder based supplement for oral administration to an individual or as an additive to food. The supplement is useful in reducing certain risk factors of cardiovascular disease. The alfalfa sprout powder based supplement is shown to be effective in reducing the levels of an individual's C-reactive protein, LDL, homocysteines and triglycerides. It is also shown to increase an individual's HDL level. See Folic Acid and Alfalfa, The Fall Study, Lawrence D. Rink, M.D., F.A.C.C., Clinical Professor of Medicine, Indiana University School of Medicine, Feb. 12, 2003, attached and incorporated herewith. As a result of these discoveries, alfalfa sprout powder based supplement, in combination with other ingredients such as Folic Acid, B-12 and B-6, can be used to reduce the risk of cardiovascular problems.

As a result of the present invention it is possible to administer the alfalfa sprout powder based supplement to reduce an individual's C-reactive protein (CRP). CRP is a marker of inflammation and high levels of CRP increases an individual's risk for future cardiac events.

According to the method of the present invention, alfalfa sprout powder based supplement is administered (e.g., capsule; along with materials necessary to form a tablet or caplet as a delivery vehicle for the alfalfa sprout powder based supplement) in sufficient quantities to reduce the "risk factors" for cardiovascular disease. The alfalfa sprout powder based supplement is administered orally, preferably with your meal.

According to another method of the present invention, alfalfa sprout powder based supplement is administered in a powder form and used as an additive during the production of all types of foods in sufficient quantities to reduce the "risk factors" for cardiovascular disease.

The present invention is also a pharmaceutical composition comprising alfalfa sprout powder based supplement in a pharmaceutically acceptable carrier, wherein the alfalfa sprout powder based supplement is present in an amount between 1000 mg-2000 mg.

In conclusion, the invention is a method of reducing certain "risk factors" of cardiovascular disease in a human patient, comprising of orally ingesting a quantity of between 1000 and 2000 mg per day of alfalfa sprout powder and folic acid, wherein the quantity is sufficient to improve and maintain health levels of C-reactive protein, LDL, HDL, homocysteines and triglycerides. The use of alfalfa sprout powder based supplement designed for use as an anti-inflammatory to reduce certain risk factors for cardiovascular disease, including LDL, HDL, C-reactive protein, homocysteines and triglycerides.

The Study.

Folic Acid and Alfalfa

The Fall Study

Background:

There have been reports that alfalfa sprouts will lower total cholesterol and LDL levels in the blood. This has not been tested in a prospective, randomized or blinded trial.

Methods and Results:

45 patients, most with known coronary artery disease and many under treatment for hyperlipidemia were selected for the study. Patients were randomly assigned to either Group A placebo, Group B low dose alfalfa, and 230 mcg of folic acid, or Group C double dose alfalfa and folic acid.

The trial was 6 weeks and all patients were instructed to follow a low fat, low cholesterol diet, perform regular exercise in moderation, and to take the medication regularly. Group A (placebo)—one capsule per day, group B-two capsules per day, and group C-two capsules twice per day.

TABLE 1

|  | Group A | Group B | Group C |
|---|---|---|---|
| LDL | 5.9% decrease | 16.6% decrease | 8.6% decrease |
| HDL | 3.2% decrease | 11.2% increase | 1.5% increase |
| C-reactive protein | 33.6% increase | 24.4% decrease | 50.4% decrease |
| Homocysteine | 5.6% increase | 11.5% decrease | 6.3% decrease |
| Triglycerides | 2.4% decrease | 1.4% decrease | 15.0% decrease |

Statement:

Cardiovascular disease is the most common cause of death and disability in the United States. More people die from cardiovascular disease than all of the other causes of death combined. Cardiovascular disease has been the most common cause of death in the United States since 1900 with the exception of the year 1918, during a flu outbreak. Multiple epidemiologic and clinical blinded prospective studies have indicated that lowering LDL levels will decrease the risk of cardiac events in primary prevention and will decrease recurrent cardiac events and decrease mortality in secondary prevention. The FDA has approved many drugs to be used in lipid lowering. Approximately 15 billions dollars per year is spent on lipid lowering medications. An equal amount of money is estimated to be spent on dietary and herbal supplements that do not require FDA approval and which are primarily directed toward lowering the risk of cardiovascular events. There are reports that alfalfa sprouts will lower serum cholesterol LDL levels and possibly raise HDL levels.

Prospective studies using diet as a means of controlling risk factors for cardiac events and decreasing cardiac events have been disappointing. The information regarding omega-3 fatty acids probably offers our best opportunity in this regard. The Adult Treatment Panel III has recommended lifestyle changes including exercise and dietary modification as a major means of lowering cardiovascular risk and future cardiac events. Among a list of emerging "risk factors" are homocysteine levels and C-reactive protein. Elevated levels of homocysteine are positively correlated with risk for CHD. Folic acid and possibly B vitamins 6 and 12 have been documented to lower homocysteine levels.

C-reactive protein (CRP) is a marker for inflammation. Coronary artery disease is an inflammatory disease and there is now substantial evidence that persons with elevated high sensitivity C-reactive protein (hs-CRP) are at increased risk for future cardiac events. Inflammation within coronary plaques leads to plaque rupture and cardiac events. Statin drugs and a healthy lifestyle are known to reduce high sensitivity C-reactive protein. The Writing group of the 2002 workshop on inflammation markers and cardiovascular disease recommended measurement of hs-CRP in conjunction with other risk factors in people with increased risk of coronary artery disease. In many studies hs-CRP has been a better predictor of future cardiac events than LDL.

With this in mind, we undertook a study to determine the effects of alfalfa sprouts and folic acid on known risk factors of coronary artery disease including total cholesterol, LDL, HDL, triglycerides, high sensitivity C-reactive protein, homocysteine levels, and apolipoprotein (b).

All patients were already under some from of treatment for hyperlipidemia. The patients were advised not to change their medication prior to enrollment to the study or during the trial. The study was first discussed with the patients and they were supplied capsules which either contained placebo, Group B 560 mg of alfalfa sprout powder and 230 mcg of folic acid, 2 capsules each day for a total of 1,120 mg alfalfa sprout powder and 460 mcg of folic acid or Group C, 2 capsules twice a day for a total of 2,240 mg of alfalfa sprout powder and 920 mcg of folic acid.

All patients underwent a history and physical exam prior to the start of the study and prior to blood samples being obtained. All patients received instruction in a low fat, low cholesterol diet, similar to the previously recommended Step 2, American Heart Association diet. All patients were instructed in exercise in moderation.

The majority of patients in this study were already following this type of lifestyle. Over 50% of the patients were already receiving statin drugs and many of the other patients were intolerant to statins because of myalgias or true rhabdomyolysis.

Many patients were already receiving folic acid.

Results:
1. All patients tolerated the medication well.
2. One patient in the placebo group stopped the medicine because she felt that the drug irritated her stomach.
3. One patient dropped out of Group C for personal reasons.
4. One patient in Group C who was taking 80 mg of an atorvastatin a day discontinued his atorvastatin during the study and therefore he had a marked increase in LDL level and his results were not included in the averages.

The results of the study were, as seen in Table 1, encouraging in that the LDL levels decreased in both treatment groups and more than in the placebo group. HDL also increased in both treatment groups and decreased in the placebo group. A surprising potential benefit of this treatment was the lowering of high sensitivity C-reactive protein levels. This has not been previously reported and the possible mechanism for this is not known, unless it is merely on the basis of lowering LDL levels. A similar lowering was not noted in the placebo group.

The results of the study are impressive since the average baseline LDL levels were only 133 and 151 in Groups B and C. The reason for a greater percentage reduction of LDL and raising HDL in Group B is not clear.

A combination of alfalfa sprout powder and folic acid appears to be a reasonable relatively inexpensive method for lowering one's risk for cardiac events. This should be tested in a larger, double blinded prospective trial to see if this not only lowers known cardiac risk factors but also lowers the number of cardiac events.

I claim:

1. A composition for lowering low-density lipoprotein cholesterol (LDL cholesterol), C Reactive protein, homocysteines and triglycerides, and increasing high-density lipoprotein (HDL cholesterol) comprising 560 mg of alfalfa sprout powder, 230 mcg of folic acid, 12.5 mg of Vitamin B-6 and 500 mcg of Vitamin B-12.

2. The composition of claim 1, wherein said composition is in an oral dosage form.

3. The composition of claim 1 further comprising a vitamin selected from the group consisting of Vitamin C, Vitamin E, Vitamin D and mixtures thereof.

4. The composition of claim 2, wherein said oral dosage form is selected from the group consisting of a chewable tablet, a quick dissolve tablet, an effervescent tablet, a hard gelatin capsule, a soft gelatin capsule, reconstitutable particles, microparticles, a suspension, an elixir, a caplet, a fortified food, a pudding, a yogurt, a gelatin, a cereal, a nutritional bar and combinations thereof.

5. The composition of claim 2, wherein in the oral dosage form is selected from the group consisting of an immediate release oral dosage form, an extended release oral dosage form, a pulse release oral dosage form, a delayed release oral dosage form, a controlled release oral dosage form and combinations thereof.

6. A method for lowering low-density lipoprotein cholesterol (LDL cholesterol), C Reactive protein, homocysteines and triglycerides, and increasing high-density lipoprotein (HDL cholesterol) comprising orally administering to an animal or human in need thereof the composition of any one of claims 1, 2, 3, 4 or 5.

7. The method of claim 6, wherein the administration occurs once during a twenty-four hour period.

8. The method of claim 6, wherein the administration occurs at least twice during a twenty-four hour period.

9. The method of claim 6, wherein the method further comprises providing indicia indicating the time period for administration.

* * * * *